(12) United States Patent
Gunzert-Marx et al.

(10) Patent No.: US 7,786,433 B2
(45) Date of Patent: Aug. 31, 2010

(54) PHANTOM AND METHOD FOR QUALITY MONITORING OF A MEDICAL SYSTEM

(75) Inventors: Konstanze Gunzert-Marx, Erlangen (DE); Sophia Knop, Erlangen (DE); Tim Use, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 232 days.

(21) Appl. No.: 12/072,989

(22) Filed: Feb. 28, 2008

(65) Prior Publication Data

US 2008/0219410 A1    Sep. 11, 2008

(30) Foreign Application Priority Data

Mar. 7, 2007   (DE) .................... 10 2007 011 154

(51) Int. Cl.
*G01D 18/00*   (2006.01)
(52) U.S. Cl. .............. 250/252.1; 250/370.07; 250/492.1; 378/18; 378/48; 378/207
(58) Field of Classification Search ........... 250/252.1, 250/306, 307, 309, 370.07, 370.08, 370.09, 250/370.1, 390.02, 390.03, 390.04, 390.06, 250/390.12, 391, 393, 492.1, 492.21, 492.3; 378/18, 48, 50–54, 65, 182, 204, 207, 208
See application file for complete search history.

(56) References Cited

U.S. PATENT DOCUMENTS

| 3,310,885 | A | * | 3/1967 | Alderson ..................... 434/267 |
| 4,163,152 | A | * | 7/1979 | Suzuki ....................... 250/374 |
| 4,460,832 | A |   | 7/1984 | Bigham |
| 5,056,130 | A |   | 10/1991 | Engel |
| 5,107,839 | A |   | 4/1992 | Houdek et al. |
| 5,416,816 | A |   | 5/1995 | Wenstrup et al. |
| 5,481,587 | A |   | 1/1996 | Mazess |
| 5,769,779 | A |   | 6/1998 | Alderson |

(Continued)

FOREIGN PATENT DOCUMENTS

DE    31 45 262 A1    5/1983

(Continued)

OTHER PUBLICATIONS

German Office Action for DE 10 2007 011 154.3-54 dated Sep. 4, 2007 and English translation.

(Continued)

*Primary Examiner*—Bernard E Souw
(74) *Attorney, Agent, or Firm*—Brinks, Hofer, Gilson & Lione

(57) ABSTRACT

A phantom for quality monitoring of a medical system, in particular a medical therapy system, or particle therapy system, is described. The phantom has a fixation device for coupling the phantom to a positioning device. In an aspect, a method for quality monitoring in a medical system, in particular a medical therapy system or particle therapy system is described, in which such a phantom is coupled via a fixation device to a positioning device and, with the aid of the positioning device, is brought to a predefined position. In another aspect, a particle therapy system has a treatment chamber, with a positioning device to which a phantom can be coupled so that the phantom can be brought to a predefined spatial position using the positioning device.

16 Claims, 6 Drawing Sheets

U.S. PATENT DOCUMENTS

| | | | |
|---|---|---|---|
| 5,799,059 A * | 8/1998 | Stembridge et al. | 378/207 |
| 5,841,835 A * | 11/1998 | Aufrichtig et al. | 378/207 |
| 6,207,952 B1 | 3/2001 | Kan et al. | |
| 6,231,231 B1 * | 5/2001 | Farrokhnia et al. | 378/207 |
| 7,252,434 B2 * | 8/2007 | Jaradat | 378/207 |
| 2005/0013406 A1 | 1/2005 | Dyk et al. | |
| 2005/0259793 A1 * | 11/2005 | Yeo et al. | 378/182 |
| 2006/0002511 A1 * | 1/2006 | Miller et al. | 378/65 |
| 2006/0219945 A1 * | 10/2006 | Jaradat | 250/492.1 |
| 2008/0219410 A1 * | 9/2008 | Gunzert-Marx et al. | 378/207 |
| 2008/0219411 A1 * | 9/2008 | Gunzert-Marx et al. | 378/207 |
| 2010/0019137 A1 * | 1/2010 | Torre et al. | 250/252.1 |

FOREIGN PATENT DOCUMENTS

| | | |
|---|---|---|
| EP | 0 514 971 A1 | 11/1992 |
| WO | WO 00/07037 | 2/2000 |
| WO | WO 2005/018735 A2 | 3/2005 |
| WO | WO 2007/012147 A2 | 2/2007 |

OTHER PUBLICATIONS

European Written Opinion dated Jul. 14, 2008 and English translation.

* cited by examiner

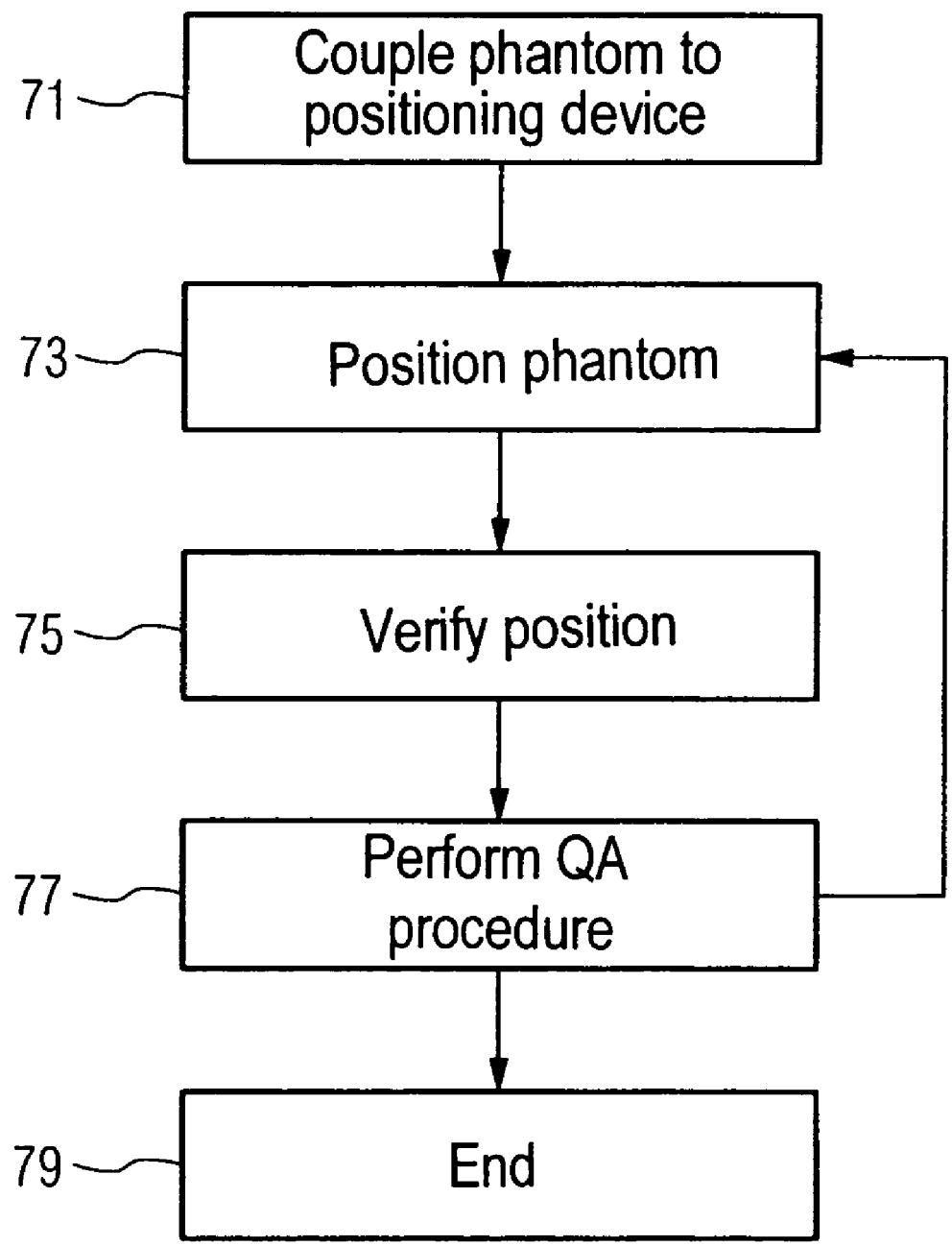

PHANTOM AND METHOD FOR QUALITY MONITORING OF A MEDICAL SYSTEM

The present application claims priority to German patent application No. DE 10 2007 011 154.3, filed on Mar. 7, 2007, which is incorporated herein by reference.

TECHNICAL FIELD

The application relates to a system for medical therapy using particles, a phantom for quality monitoring, and a method for using the same.

BACKGROUND

Particle therapy is employed particularly for radiation treatment of tumor tissue in humans. For the radiation treatment, ions such as protons, helium ions, pions, carbon ions, or other types of ions can be employed. In comparison to conventional radiation treatment with photons or electrons, radiation treatment with ions is characterized by the fact that the penetration depth of the radiation into the human tissue can be controlled more precisely. This makes more-precise radiation treatment of the tumor possible, and, in the treatment, the surrounding tissue that is to be spared can be better protected from the radiation.

For radiation treatment, the ions are accelerated to high energies in an accelerator system which, for instance, includes a synchrotron or cyclotron, and are aimed in a beam at the body to be treated. The beam is deflected and controlled by a magnet system. Parameters of the beam that are essential and relevant for safety are dependent essentially on the settings at the system. The parameters determine the beam properties. These include, among others, the beam diameter, the beam position, and the energy of the beam.

The properties of the particle beam used for the therapy must be known and controlled. To ensure this, quality assurance (QA) procedures (also called QA procedures; quality control (QC), or similar terminology may also be used) are performed at regular intervals.

The monitoring of the beam properties is performed, for example, with so-called "phantoms". Such phantoms are irradiated with the particle beam and have a sensitive unit with which the interaction of the particle beam with the phantom can be measured and monitored. The sensitive units are typically films, which are exposed to irradiation by the particle beam. However, depending on the type of phantom, detectors of other types may also be used, such as ionization chambers or thimble chambers.

Until now, for monitoring various beam parameters at different intervals, different phantoms have each been employed. For each QA procedure, the phantom used must be put in a defined position relative to the beam, so that for different phantoms, positioning must be done for each one, thus requiring repeated manual interventions. Hence in phantoms in which a film, such as an X-ray film, is used as the sensitive unit, a separate film is used, developed and evaluated for each QA procedure and for each phantom.

SUMMARY AND DESCRIPTION

A phantom for quality monitoring of a medical system, having a fixation device for coupling or mounting the phantom to a positioning device is described. The phantom is for use in a therapy system, such as a particle therapy system. With the aid of the fixation device and of the coupling of the phantom to a positioning device, positioning of the phantom in space is facilitated. The phantom can be mounted in a defined position relative to the positioning device with the fixation device. The step of positioning can now be done more simply, precisely, replicably, and repeatably.

The fixation device may couple the phantom to a movable positioning device. As a result, repositioning of the phantom in space can be performed by way of the positioning device. The positioning device is embodied as a robot arm, and in particular as an automatically controlled robot arm. The setpoint position or positions of the phantom in space may for instance be stored in as data in a memory of a computer in the control system of the robot arm, so that positioning of the phantom can be done automatically in a precise and replicable way.

Depending on the type or types of phantom used, a specific property of the particle beam can be monitored, such as the energy of the particle beam, the extent of the particle beam, or the position of the particle beam. Depending on the phantom type, the evaluation of the measured beam parameters can be done during the performance of the associated QA procedure ("on-line"), or after the performance of the associated QA procedure ("off-line").

The positioning device used may be a patient positioning device. A patient positioning device is typically already present in treatment chambers of a particle therapy system, so that this patient positioning device can be used for positioning the phantom without requiring an additional positioning device.

The phantom has a mount capable of accommodating at least one phantom unit. Phantom units may be sized and dimensioned so as to be interchangeably mounted to the phantom. As a result, the phantom can be employed flexibly, since different phantom units for monitoring different beam qualities or beam parameters can be secured in the mount, which may be, for example, a mounting frame.

As a result, the same phantom can be used for different QA procedures. With each phantom unit, a specific QA procedure may be performed. As a result, with the one phantom, and more than one mountable phantom unit, a number of different QA procedures can be performed.

The phantom has a further mounting for receiving a film unit. Part of the phantom, which may be in a part of the mount, may be a so-called "wedge phantom". The phantom may also be sized and dimensioned so as to receive an ionization chamber.

A portion of the phantom, which may be the mount, may have at least one position marking. With the aid of this kind of position marking, positioning of the phantom in space can be monitored, for example, by projecting the desired position of the phantom in space onto the phantom with the aid of a fan laser beams. The pattern of the laser beams on the phantom may then be compared with the position marking, visually or automatically.

In a method for quality monitoring of beam properties in a particle therapy system, a phantom is coupled to a positioning device via a mounting device and is brought to a predefined position with the aid of the positioning device. The phantom is thus oriented and disposed in a defined relationship to the positioning device, so that replicable and precise positioning of the phantom in space can be achieved. The positioning device may be actuated so that positioning of the phantom at a predefined position can be performed automatically. The positioning device may be a robot arm and the positioning device may be triggered for actuation.

The phantom has a mounting for receiving a plurality of phantom units and may be positioned successively at various predefined spatial positions with the aid of the positioning device. The predefined positions may each be adapted to the position of the phantom units in the mounting so that, at each of the predefined positions, a respective quality monitoring of certain beam parameters is performed. The beam parameters that are being monitored depend upon the particular phantom unit with which the quality monitoring is performed. Where the phantom has at least one position marking, the positioning of the phantom at the predefined position or positions may be monitored with the aid of the position marking. For instance, a system of laser beams that is installed in the treatment room or chamber can mark three-dimensional coordinates that indicate a correct position of the phantom. The agreement of the correct position of the phantom with the actual position of the phantom may be monitored for instance by a visual or automatic calibration of the pattern of the laser beams with the position marking.

A particle therapy system can have a treatment chamber which includes a positioning device to which a phantom for the quality monitoring can be coupled. The phantom can be put at a predefined position via the positioning device.

BRIEF DESCRIPTION OF THE DRAWINGS

FIG. 6 shows method steps of an embodiment for performing a QA procedure.

DESCRIPTION

Exemplary embodiments may be better understood with reference to the drawings, but these examples are not intended to be of a limiting nature. Like numbered elements in the same or different drawings perform equivalent functions. When a specific feature, structure, or characteristic is described in connection with an example, it will be understood that one skilled in the art may effect such feature, structure, or characteristic in connection with other examples, whether or not explicitly stated herein.

The examples of diseases, syndromes, conditions, and the like, and the types of treatment protocols described herein are by way of example, and are not meant to suggest that the method and apparatus is limited to those named, or the equivalents thereof. As the medical arts are continually advancing, the use of the methods and apparatus described herein may be expected to encompass a broader scope in the diagnosis and treatment of patients.

Embodiments of this invention may be implemented in hardware, firmware, software, or any combination thereof, and may include instructions stored on a machine-readable medium, which may be read and executed by one or more processors.

Figure 1:
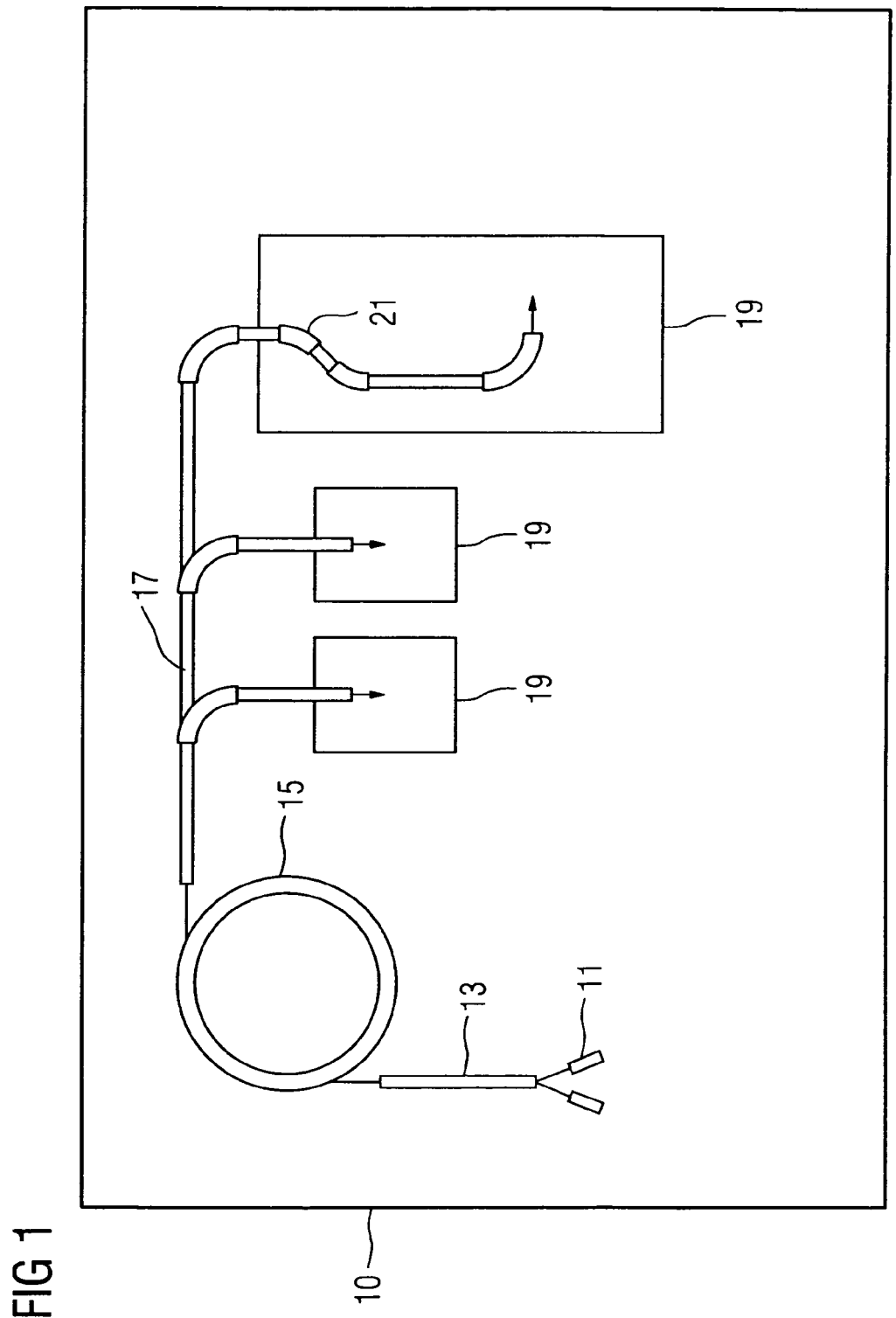
FIG. 1 shows a schematic overview of the construction of a particle therapy system in one embodiment.

FIG. 1 shows a schematic overview of the construction of a particle therapy system 10. In a particle therapy system 10, radiation treatment, particularly of diseased tissue involving tumors may be performed with a particle beam. Ions, such as protons, pions, helium ions, carbon ions, or other types of ions, may be used as the particles.

Such particles may be generated, for example, in a particle source 11 and accelerated in a preaccelerator 13, such as a linear accelerator (LINAC). The particles may then be introduced into an accelerator 15, such as a Synchrotron or Cyclotron, in which they are accelerated to energies used for the radiation treatment. Once the particles leave the accelerator 15, a beam transport system 17 carries the particle beam to the desired treatment chamber 19. In a treatment chamber 19, the accelerator particles are aimed at the body of a patient to be treated. Depending on the design of the system, this is done from a fixed direction (in so-called "fixed-beam" chambers), or from various directions using a movable rotatable gantry 21.

Figure 2:
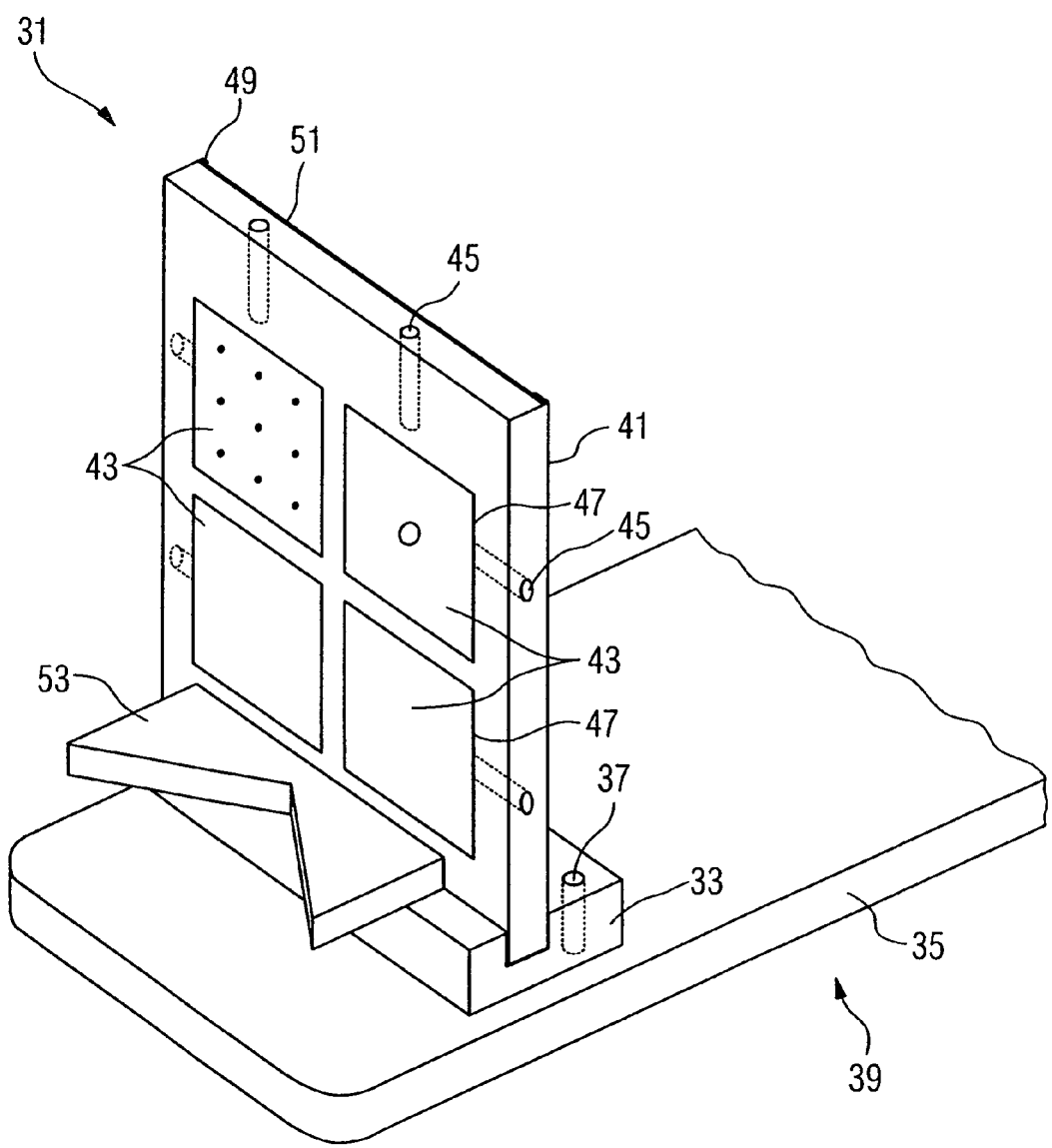
FIG. 2 shows a perspective view of one embodiment of a phantom.

FIG. 2 shows a perspective view of a phantom 31 that can be used in the context of QA procedures in a particle therapy system 10. In the base region of the phantom 31, there is a fixation device 33 which may be used to affix the phantom 31 to, for example a table 35 of a patient positioning device 39. The affixation may be, for example, by way of screws 37, by clamps, a rod and holes, or in other ways. Using the patient positioning device 39, the phantom 31 can be automatically moved to one or more predefined positions that are stored in a computer memory: for example, in the control system processor of the particle therapy system 10.

The phantom 31 may have a mounting frame 41, in which various phantom units 43 can be secured interchangeably. In the phantom 31 of the example as shown, four different phantom units 43 may be placed in the mounting frame 41 and secured via screws 45. Other fasteners may also be used.

In the mounting frame 41, the recesses 47 in which the phantom units 43 can be placed are identical, so that the phantom units 43 can easily be exchanged with one another, or replaced by one another. The phantom 31 may also have a further mounting 49, in which a film 51 can be placed. As a result, the film 51 is held in a defined position relative to the mounting frame 41, which makes the evaluation developed exposed film 51 simpler.

The lower part of the phantom 31 may have a so-called "wedge" phantom unit 53. The wedge phantom unit 53 may be replaceably secured on the mounting frame 41. The fasteners used may be the same or similar to those previously described.

Figure 3:
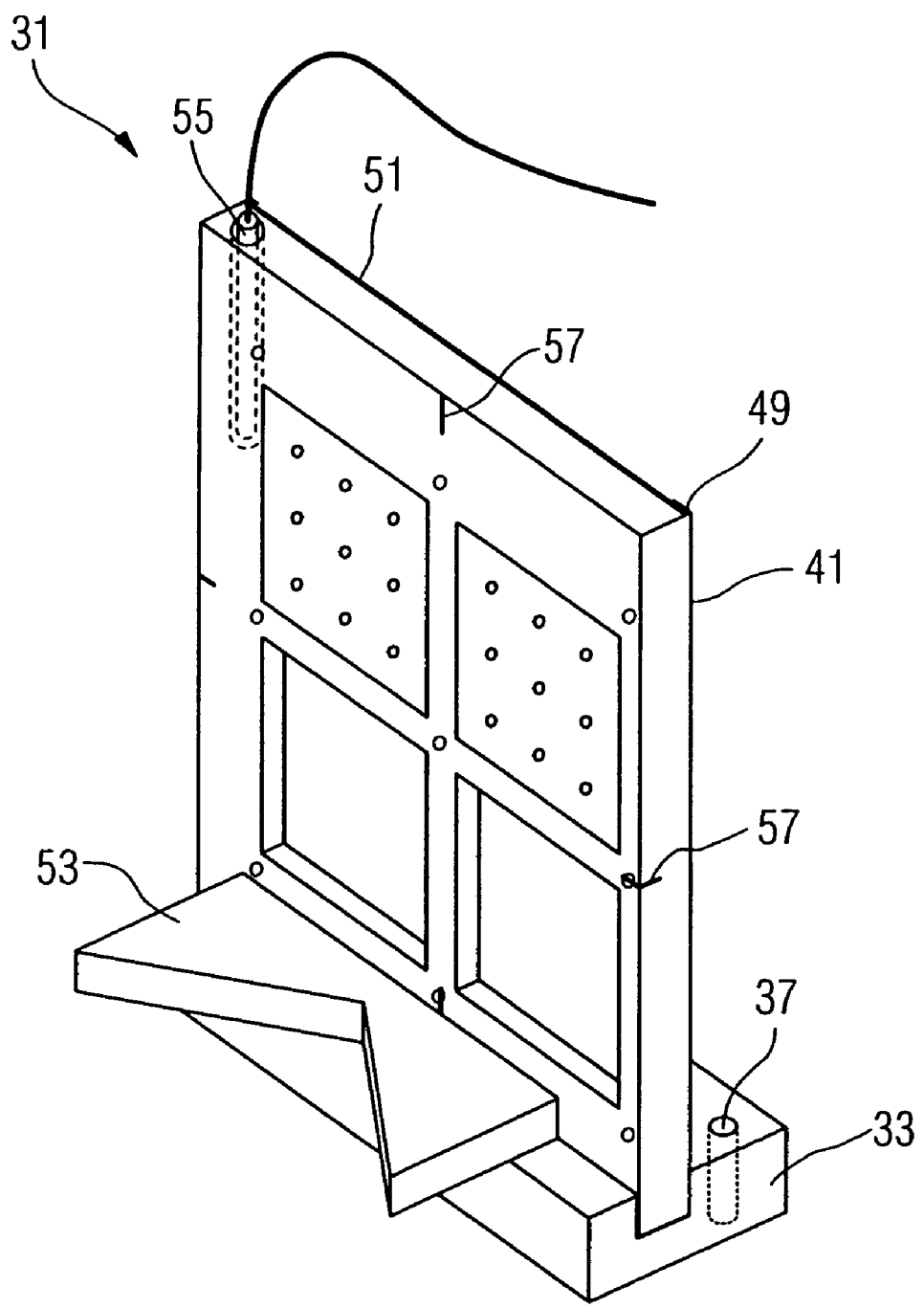
FIG. 3 shows a perspective view of a further phantom according to another embodiment.

FIG. 3 shows a perspective view of another phantom 31. An opening is provided in the mounting frame 41 of the phantom 31, into which an ionization chamber 55, which may be a thimble chamber, may be placed. The opening may, for example, be made outside the region that is covered by the film 51, so that the ionization chamber 55 does not appear in the image on the film 51.

In addition, position markings 57, with which a positioning of the phantom can be monitored, are disposed on the mounting 41 of the phantom 31. For instance, laser beams can be used to mark coordinates in space, which identify the correct position of the phantom 31 in space. From a visual inspection, with the aid of the position markings 57, monitoring can be done as to whether the position markings 57 coincide with the coordinates that are marked by the laser fans. This monitoring can also be performed automatically using, for example photodetectors, or imaging devices, such as cameras.

Figure 4:
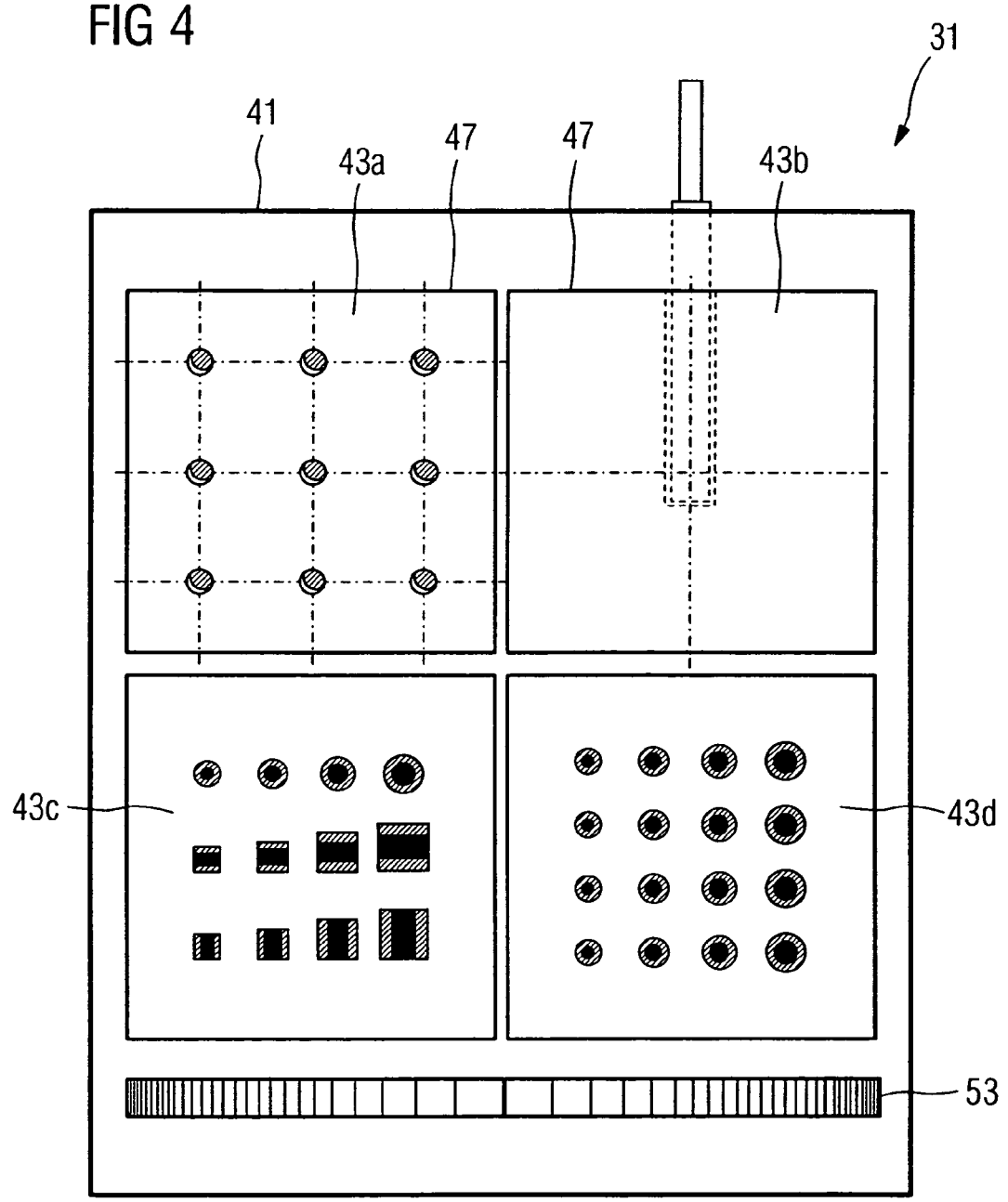
FIG. 4 shows a front view of a further embodiment of a phantom.

FIG. 4 shows a view from the front of another phantom 31. Here the phantom 31 has a rectangular surface approximately 265 mm by 325 mm, which corresponds to the size of a conventional photosensitive film presently on the market. The mounting frame 41 has four recesses 47, and one phantom unit 43a . . . 43d may be placed into each of them. Not all of the phantom units may be installed.

The four phantom units 43 may be configured to serve to monitor different properties of the particle beam with regard to its quality or constancy. For example, with a first phantom unit 43a, the precision of the position of the particle beam in the scanning region may be verified, a second phantom unit 43b may serve to monitor the air density correction in the ionization dosimetry, a third phantom unit 43c may serve to monitor the field geometry; and, a fourth phantom unit 43d may serve to monitor the focal width of the particle beam. The gray-shaded regions of the third and fourth phantom units 43c, 43d identify a Gaussian shape in the blackening of the film.

A wedge phantom 53 is mounted in the base region, and its wedgelike thickness is indicated in the drawing by vertical lines, where the spatial density of the shading lines is proportional to the thickness of the wedge. For simplicity, the fixation device 33 of the phantom 31 is not shown in FIG. 4.

The individual QA procedures for various beam parameters may be performed successively using the phantom 31, by positioning the phantom 31, with the aid of the positioning device 39, in such a way that one of the phantom units 43a . . . 43d is located in the scanning region of the particle beam. Once one QA procedure with this phantom unit has been concluded, the phantom units are repositioned with the aid of the positioning device 39, and then a further QA procedure is performed with a further one of the phantom units 43a . . . 43d. The repositioning of the phantom 31 is may be done automatically with the aid of the positioning device 39, and the control commands and location data may be stored in the memory of a processor.

Figure 5:
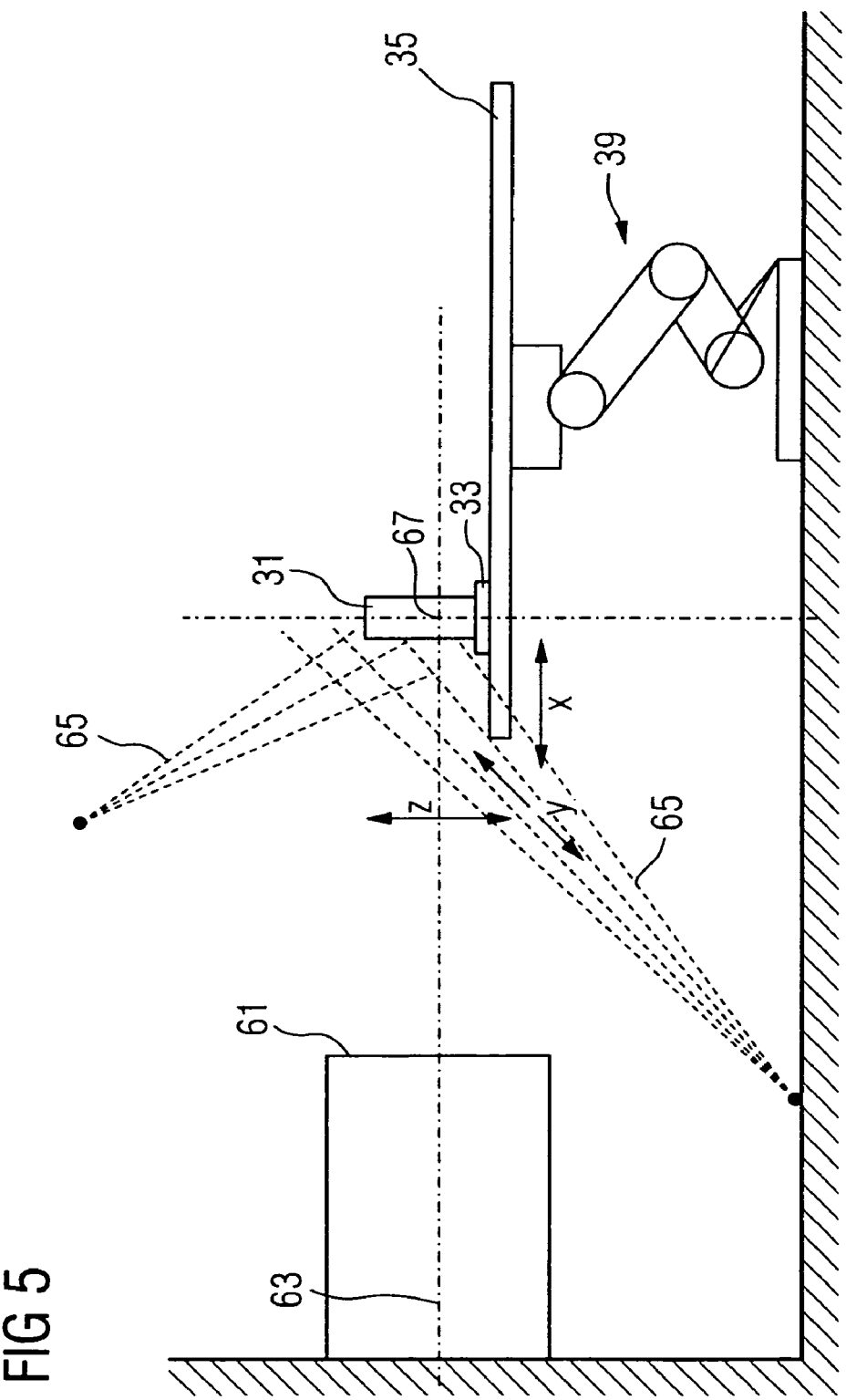
FIG. 5 shows one embodiment of the positioning of a phantom based on a patient positioning device in a treatment chamber.

FIG. 5 shows a schematic overview of a treatment chamber where the positioning device 39 is as a robot arm. The particle beam exits the beam delivery unit 61 along the beam axis 63, by way of a so-called nozzle, or aperture.

The phantom 31 is coupled via the fixation device 33 to the treatment table 35, for example, or its tabletop, and maybe three-dimensionally positioned using the patient positioning device 39. Laser beams 65 may indicate the coordinates at which the phantom is to be positioned. On the basis of the laser beams 65 and the position markings 57 on the phantom 31, the correct positioning can be monitored for instance visually or automatically using suitable detectors. In an example, the phantom 31 may be positioned at the approximate isocenter 67 of the treatment chamber.

FIG. 6 shows a schematic flow of a QA method that may be performed with a phantom. The method may include: a step 71, where the phantom 31 is coupled via the fixation device 33 to a positioning device 39, which may be a patient positioning device; a step 73, where the phantom 31 is positioned in the treatment chamber with the aid of the positioning device 39 in such a way that one of the phantom units 43 is located in the scanning region of the particle beam; a step 75, where the position of the phantom 31 in space may, optionally, be monitored with the aid of position markings 57 and laser beams 65; and a step 77, where a QA procedure for which the phantom unit 43 is appropriate, is performed.

In an aspect, steps 73, 75, 77 may be repeated until such time as all the desired QA procedures have been performed.

Using the phantom 31 with the associated positioning system 39, a plurality of QA procedures may be performed with a single phantom 31 and a single film, and the positioning of the various phantom units 43 may be done automatically, so that overall there are economies of time, material, and manual interventions.

While the method disclosed herein have been described and shown with reference to particular steps performed in a particular order, it will be understood that these steps may be combined, sub-divided, or reordered to from an equivalent method without departing from the teachings of the present invention.

Although only a few exemplary embodiments of this invention have been described in detail above, those skilled in the art will readily appreciate that many modifications are possible in the exemplary embodiments without materially departing from the novel teachings and advantages of the invention. Accordingly, all such modifications are intended to be included within the scope of this invention as defined in the following claims.

What is claimed is:

1. A phantom for quality monitoring of a particle therapy system, the phantom comprising:
   a fixation device for coupling the phantom to a positioning device, the positioning device being adapted to bring the phantom into a plurality of predefined positions with respect to a particle beam; and
   a mounting for receiving a plurality of phantom units, each of the plurality of phantom units being adapted to monitor a different beam property of the particle beam.

2. The phantom of claim 1, wherein the fixation device is configured to mount the phantom to the positioning device, the positioning device comprising a movable positioning device.

3. The phantom of claim 2, wherein the movable positioning device is a robot arm.

4. The phantom of claim 1, wherein the fixation device is configured to mount the phantom to a patient positioning device.

5. The phantom of claim 1, wherein the mounting is configured to interchangeably receive at least one of the plurality of phantom units.

6. The phantom of claim 1, wherein the phantom has a further mounting configured to receive a film unit.

7. The phantom of claim 1, wherein a portion of the phantom is a wedge phantom unit, or a further portion of the phantom is configured to receive an ionization chamber.

8. The phantom of claim 1, wherein the phantom has at least one position marking.

9. A method for quality monitoring of a particle therapy system, the method comprising:
   mounting a phantom to a positioning device using a fixation device;
   positioning the phantom using the positioning device so that the phantom is brought to a plurality of predefined positions relative to a particle beam; and
   performing quality monitoring of radiation therapy beam parameters,
   wherein the phantom has a mounting configured to receive a plurality of phantom units, each of the plurality of phantom units being adapted to monitor a different beam property of the particle beam, and
   wherein positioning the phantom comprises positioning the plurality of phantom units successively at the plurality of predefined positions relative to the particle beam.

10. The method of claim 9, wherein the positioning device is automatically positioned by a robot arm.

11. The method of claim 10, wherein the positioning device is a patient positioning device.

12. The method of claims 9, wherein the phantom has at least one position marking, and the desired positioning of the phantom at a predefined position is verified with the aid of the position marking.

13. A medical treatment system, the system comprising:
a particle therapy apparatus, the particle therapy apparatus comprising:
- a movable positioning device; and
- a phantom attached to the movable positioning device, wherein the movable positioning device is adapted to bring the phantom into a plurality of predefined positions with respect to a particle beam, and
wherein the phantom is configured to accept a plurality of phantom units, each of the plurality of phantom units being adapted to monitor a different beam property of the particle beam.

14. The medical treatment system of claim 13, wherein the particle therapy apparatus further comprises an ion generator and an ion accelerator to produce an ion beam.

15. The medical treatment system of claim 14, wherein the movable positioning unit is a robot, the robot configured to accept commands so as to position the phantom unit to measure a parameter of the ion beam.

16. The medical treatment system of claim 15, wherein the robot is a patient support table.

* * * * *